United States Patent [19]

Ramey et al.

[11] 4,069,196
[45] Jan. 17, 1978

[54] PIPERIDYL ESTERS OF HIGHER DI-TRI-, AND POLYBASIC ALIPHATIC CARBOXYLIC ACIDS AS STABILIZERS FOR POLYMERIC MATERIALS

[75] Inventors: Chester E. Ramey, Spring Valley; John J. Luzzi, Carmel, both of N.Y.

[73] Assignee: Ciba-Geigy Corporation, Ardsley, N.Y.

[21] Appl. No.: 676,431

[22] Filed: Apr. 13, 1976

[51] Int. Cl.$^2$ .......................... C07D 11/06; C08K 5/34
[52] U.S. Cl. .......................... 260/45.8 N; 260/293.63; 260/293.64
[58] Field of Search ...................... 260/45.8 N, 293.63, 260/293.64

[56] References Cited

U.S. PATENT DOCUMENTS

| 3,640,928 | 2/1972 | Murayama et al. | 260/45.8 N |
| 3,840,494 | 10/1974 | Murayama et al. | 260/45.8 N |
| 3,984,371 | 10/1976 | Murayama et al. | 260/45.8 N |

Primary Examiner—Donald E. Czaja
Assistant Examiner—H. H. Fletcher
Attorney, Agent, or Firm—Nestor W. Shust

[57] ABSTRACT

Piperidyl esters of the formula

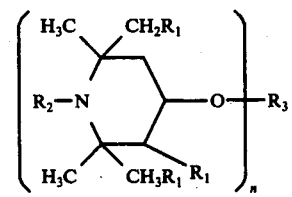

wherein $R_1$ is hydrogen or lower alkyl, $R_2$ is hydrogen, oxyl alkyl, alkenyl, alkinyl, alkoxy-alkyl, aralkyl or lower acyl and $n$ is 2 or 3, and when $n$ is 2, $R_3$ is a diacyl of 36 carbons and when $n$ is 3, $R_3$ is a triacyl of 37 to 54 carbons. These compounds are useful as light stabilizers of polymeric materials.

16 Claims, No Drawings

PIPERIDYL ESTERS OF HIGHER DI-TRI-, AND POLYBASIC ALIPHATIC CARBOXYLIC ACIDS AS STABILIZERS FOR POLYMERIC MATERIALS

BACKGROUND OF THE INVENTION

Acyl piperidyl compounds are disclosed in U.S. Pat. Nos. 3,120,540; 3,640,928 and 3,840,494. U.S. Pat. No. 3,120,540 discloses piperidyl esters of lower dicarboxylic acids having 3 to 6 carbon atoms and quaternary ammonium salts thereof which are pharmacologically active in lowering blood pressure. U.S. Pat. Nos. 3,640,928 and 3,840,494 disclose piperidyl esters of aliphatic, alicyclic, aromatic or heterocyclic dicarboxylic acids. Other related compounds are disclosed in British Pat. No. 1,399,239. These compounds are said to be useful as stabilizers against photo and thermal deterioration of synthetic polymeric materials. U.S. Pat. No. 3,840,494. Thus although piperidyl esters in general have been known, it has now been found that surprisingly and unexpectedly the piperidyl esters of certain acids possess certain unusual properties as compared to the prior art compounds.

DETAILED DISCLOSURE

The compounds of this invention are directed to piperidyl esters of the formula

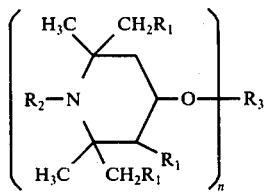

I wherein $R_1$, is hydrogen or a lower alkyl group of 1 to 5 carbons, $R_2$ is hydrogen, oxyl, alkyl having 1-12 carbon atoms, alkoxyaklyl of 2 to 21 carbons, alkenyl of 3 to 6 carbons, alkinyl of 3 to 6 carbons benzyl or benzyl substituted by alkyl groups of 1 to 4 carbons, or aryl derived from a saturated or unsaturated aliphatic acid of 1 to 4 carbons or aliphatic cycloaliphatic or aromatic carbamic acid of the formula —CO—NH—R or aliphatic, cycloaliphatic or aromatic carbonic acid half ester of the formula -COOR where R is alkyl of 1 to 6 carbons, $n$ is an integer from 2, or 3 when $n$ is 2, $R_3$ is a diacyl group derived from a straight or branched chain aliphatic or alicyclic, saturated or unsaturated carboxylic acid, having 36 carbon atoms;

when $n$ is 3, $R_3$ is a tri-acyl group derived from a straight or branched chain aliphatic or alicyclic saturated or unsaturated carboxylic acid having from 37 to 54 carbon atoms.

Preferably $R_1$ is hydrogen or methyl and most preferably hydrogen and $R_2$ is hydrogen, lower alkyl containing 1-4 carbon atoms, or lower acyl containing 1-4 carbon atoms, and most preferably hydrogen or methyl.

When $n$ is 2, $R_3$ is preferably derived from an alicyclic dicarboxylic acid which contains alkyl, alkenyl, carboxyalkylene and/or carboxyalkenylene substituents on the unsaturated six membered alicyclic ring, said acid having 36 carbon atoms. A specific structural illustration of such an acid is as follows:

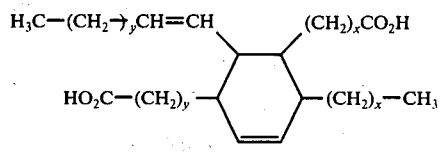

where $x + Y = 12$ and $x$ and $y$ is each an integer of 3 to 9. Of course, it must be understood that even in the above depicted structure the various substituents may be located at different positions on the ring. When $n$ is 3, $R_3$ is preferably a triacyl group derived from an alicyclic tricarboxylic acid which contains alkyl and carboxyalkyl substituents on the unsaturated six-membered alicyclic rings, said acid having 37 to 54 carbon atoms and two alicyclic rings. A specific structural illustration of such an acid is as follows:

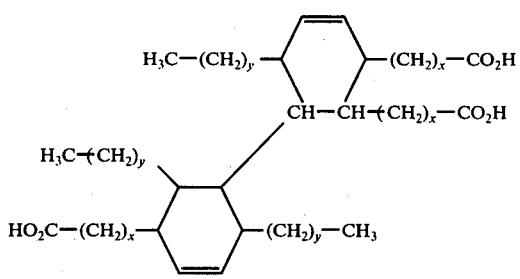

where $x$ and $y$ are as defined above.

It should be noted that the di and tri acids employed in the preparation of the compounds of this invention are generally not pure materials. Such polyacids usually contain a small amount of closely related acids which either have shorter chains and/or have higher or lower acid functionality. This results from the process employed in preparing the polyacids. For example, $C_{36}$ diacid is prepared by the Diels-Alder dimerization of linoleic and/or oleic acids which yields the commercially available product EMPOL 1010 (Emery Industries). The tri basic acids are prepared basically in the same manner by appropriately controlling the reaction (see Goebel, J. Am. Oil Chem. Sec. 24, p. 65 and U.S. Pat. No. 2,482,761). Therefore such polybasic acids are really mixtures of mono, di and tri functional acids. For example, the noted commercially available products have the following approximate compositions: EMPOL 1054-A: 4% $C_{18}$ monobasic acid, 55% $C_{36}$ dibasic acid and 35% $C_{54}$ tribasic acid; EMPOL 1040 trimer acid: 20% $C_{36}$ dibasic acid and 80% $C_{54}$ tribasic acid; EMPOL 1041 trimer acid: 10% $C_{36}$ dibasic acid and 90% $C_{54}$ tribasic acid. Di and tribasic acids of somewhat different chain lengths, chain branching and relative proportions of mono, di and triacids can be prepared by known methods and employed in preparing the compounds of this invention, but the above noted acid mixtures are preferred since they are commercially available at this time.

Two general synthetic procedures can be used in preparing the compounds of this invention.

a. Direct esterification of the di-acid or tri-acid with the piperidinol using a neutral catalyst such as titanium tetraisopropylate or dibutyltinoxide with a high boiling aromatic solvent such as xylene or mesitylene with azeotropic removal of water.

b. Trans-esterification of a preformed lower alkyl ester of the di- or triacid with the piperidinol using a solvent boiling the higher than the lower aliphatic alcohol or a solvent in which the alcohol is immissible at room temperature and a basic catalyst such as lithium amide.

The piperidinols may be prepared similar to procedures presented in the published German Patent Application DT-OS No. 2,352,658, especially by reducing a corresponding 4-ketone by catalytic hydrogenation or for example with sodium borohydride or lithium aluminum hydride. The corresponding 4-ketone can be prepared by reacting an aliphatic ketone, this being acetone or a higher homolog of acetone with ammonia, e.g. 2,3,6-trimethyl 1,6-diethyl piperidin-4- one is obtained from methyl-ethyl ketone and ammonia, similar to W. Traube in Chem. Ber. 41, 777 (1908). The corresponding 4-ketone can also be obtained by hydrolysis of an alkylsubstituted tetrahydropyrimidine in the presence of an acid catalyst, similar to U.S. Pat. No. 3,513,170. The corresponding 4-ketone having different substituents in the 2- and 6- positions can be obtained by reacting first a ketone $R_4$—CO—$R_5$ with ammonia and hydrolyzing the formed pyrimidine derivative to give an amino ketone $H_2N$—$C(R_4R_5)$ $CH(R_6)$—$COCH_2R_7$ as described in Helvet. Chim. Acta 30, 1115 (1947). In a second step this amino ketone is reacted with ammonia and a second ketone $R_1$—CO—$R_{21}$ resulting in a pyrimidine derivative as described in Monatshefte Chemie 88, 464 (1957). From this the 4-ketone can be obtained by hydrolysis. Similar methods in preparing alkylated 4-piperidones are described in published German Patent Application Nos. 2,429,745, 2,429,746, 2,429,935, 2,429,936 and 2,429,937.

Compounds of the type wherein $R_1$ and $R_2$ are together lower alkylene having 4 or 5 carbon atoms and $R_4$ and $R_5$ are methyl or together lower alkylene having 4 or 5 carbon atoms may be prepared by the procedure of T. Yoshioka, S. Higashida, and K. Murayama, Bull. Chem. Soc. Japan 45 636-638(1972) and subsequent reduction of the ketone by catalytic hydrogenation or with sodium borohydride or lithium aluminum hydride to the corresponding piperidin-4-ol. The resulting alcohol is then reacted with a di or polyacid according to one of the procedures mentioned above to yield compounds of this invention.

Illustrative examples of the compounds of this invention are given below:

$C_{36}$ "Dimer Acid" diester of 2,2,6,6-tetra-methyl-piperidinol poly (2,2,6,6-tetramethylpiperidyl-4)ester of polybasic acid $C_{54}$ "Trimer Acid" triester of 2,2,6,6-tetramethylpiperidin-4-ol The compounds of this invention can effectively stabilize a wide range of organic polymers against light-induced deterioration with superior compatibility with polymer substrates. Polymers which can be stabilized in this way include:

1. Polymers which are derived from mono- or diolefins, e.g., polyethylene which can optionally be crosslinked, polypropylene, polyisobutylene, polymethylbutene-1, polymethylpentene-1, polyisoprene, polybutadiene.
2. Mixtures of the homopolymers cited under 1), for example mixtures of polypropylene and polyethylene, polypropylene and polybutene-1, polypropylene and polyisobutylene.
3. Copolymers of the monomers based on the homopolymers cited under 1), for example ethylene/propylene copolymers, propylene/butene-1 copolymers, propylene/isobutylene copolymers, ethylene/butene-1 copolymers as well as terpolymers of ethylene and propylene with a diene, for example hexadiene, dicyclopentadiene or ethylidene norbornene, and copolymers of α-olefins, e.g., ethylene, with acrylic or methacrylic acid.
4. Polystyrene.
5. Copolymers of styrene and of α-methylstyrene, for example styrene/butadiene copolymers, styrene/acrylonitrile copolymers, styrene/acrylonitrile/methylacrylate copolymers, styrene/acrylonitrile/acrylic ester copolymers, styrene/acrylonitrile copolymers modified with acrylic ester polymers to provide impact strength as well as block copolymers, e.g., styrene/butadiene/styrene block copolymers.
6. Graft copolymers of styrene, for example the graft polymer of styrene to polybutadiene, the graft polymer of styrene with acrylonitrile to polybutadiene as well as mixtures thereof with the copolymers cited under 5), commonly referred to as acrylonitrile/butadiene/styrene or ABS plastics.
7. Halogen-containing vinyl polymers, for example polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, vinylidene chloride/vinyl acetate copolymers.
8. Polymers which are derived from α,β-unsaturated acids and derivatives thereof, polyacrylates and polymethacrylates, polyacrylic amides and polyacrylonitrile.
9. Polymers which are derived from unsaturated alcohols and amines and from the acyl derivatives thereof or acetals, for example polyvinyl alcohol, polyvinyl acetate, polyvinyl stearate, polyvinyl benzoate, polyvinyl maleate, polyvinyl butyral, polyallyl phthalate, polyallyl melamine and copolymers thereof with other vinyl compounds, for example ethylene/vinyl acetate copolymers.
10. Homopolymers and copolymers which are derived from epoxides, for example polyethylene oxide or the polymers which are derived from bis-glycidyl ethers.
11. Polyacetals, for example polyoxymethylene, as well as polyoxymethylenes which contain ethylene oxide as comonomer.
12. Polyalkylene oxides, for example polyoxyethylene, polypropylene oxide or polyisobutylene oxide.
13. Polyphenylene oxides.
14. Polyurethanes and polyureas.
15. Polycarbonates.
16. Polysulphones.
17. Polyamides and copolyamides which are derived from diamines and dicarboxylic acids and/or from aminocarboxylic acids or the corresponding lactams, for example polyamide 6, polyamide 6/6, polyamide 6/10, polyamide 11, polyamide 12, poly-m-phenylene-isophthalamide.
18. Polyesters which are derived from dicarboxylic acids and dialcohols and/or from hydroxycarboxylic acids or the corresponding lactones, for example polyethylene glycol terephthalate, poly-1,4-dimethylol-cyclohexane terephthalate.
19. Cross-linked polymers which are derived from aldehydes on the one hand and from phenols, ureas and melamines on the other, for example phenol-/formaldehyde, urea/formaldehyde and melamine-/formaldehyde resins.
20. Alkyd resins, for example glycerol/phthalic acid resins and mixtures thereof with melamine/formaldehyde resins.
21. Unsaturated polyester resins which are derived from copolyesters of saturated and unsaturated dicarboxylic acids with polyhydric alcohols as well as from vinyl compounds as cross-linking agents and also the halogen-containing, flame-resistant modifications thereof.
22. Natural polymers, for example cellulose, rubber, as well as the chemically modified homologous derivatives thereof, for example cellulose acetates, cellulose propionates and cellulose butyrates and the cellulose ethers, for example methyl cellulose.

From these the polymers of groups 1 – 6, 14 and 17 are of particular interest as the application of the stabilizers according to the invention has an outstanding effect on these polymers.

The amount of a stabilizer of formula I needed for effective stabilization of the synthetic polymer will depend on a variety of factors, such as the type and properties of the polymer concerned, its intended use, and the presence of other stabilizers. It is generally satisfactory to use from 0.01 to 5% by weight of the stabilizers of formula I, based on the weight of the organic polymer, but the most effective range will vary with the type of polymer: viz 0.01 to 2.0%, preferably 0.02 to 1.0%, by weight for olefin, diene and styrene polymers; 0.01 to 1.0%, preferably 0.02 to 0.5%, by weight for vinyl chloride and vinylidene chloride polymers; and 0.01 to 5.0%, preferably 0.02 to 2.0%, by weight for polyurethanes and polyamides. If desired, two or more of the stabilizers of formula I may be used together.

The stabilizers of formula I may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer.

The stabilized polymer compositions of the invention may optionally also contain various conventional additives, such as the following:

PHENOLIC ANTIOXIDANTS

1. Single 2,6-dialkylphenols, such as 2,6-di-tert.-butyl-4-methylphenol, 2,6-di-tert.-butyl-4-methoxymethylphenol or 2,6-di-tert.-butyl-4-methoxyphenol.
2. Bisphenols, such as 2,2'-methylene-bis-(6-tert.-butyl-4-methylphenol), 2,2'-methylene-bis-(6-tert.-butyl-4-ethylphenol), 2,2'-methylene-bis-[4-methyl-6-(α-methylcyclohexyl)-phenol], 1,1-bis-(5-tert.-butyl-4-hydroxy-2-methylphenyl)-butane, 2,2-bis-(5-tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercapto-butane, 1,1,5,5-tetra-(5-tert.-butyl-4-hydroxy-2-methylphenyl)-pentane, ethylene glycol-bis-[3,3-bis-(3'-tert.-butyl4'-hydroxyphenyl)-butyrate], 1,1-bis-(3,5-dimethyl-2-hydroxyphenyl)-3-(n-dodecylthio)-butane, or 4,4'-thio-bis-(6-tert.-butyl-3-methylphenol).
3. Hydroxybenzyl aromates, such as 1,3,5-tri-(3,5-di-tert.-butyl-4-hydroxybenzyl)-2,4,6-trimethylbenzene, 2,2-bis-(3,5-di-tert.-butyl-4-hydroxybenzyl)-malonic acid-dioctadecyl ester, 1,3,5-tris-(3,5-di-tert.-butyl-4-hydroxybenzyl)-isocyanurate, or 3,5-di-tert.-butyl-4-hydroxybenzyl-phosphonic aciddiethyl ester.
4. Amides of β-(3,5-di-tert.-butyl-4-hydroxyphenyl)-propionic acid, such as 1,3,5-tris-(3,5-di-tert.-butyl-4-hydroxyphenyl-propionyl)-hexahydro-s-triazine, N,N'-di-(3,5-di-tert.butyl-4-hydroxyphenyl-propionyl)-hexamethylenediamine.
5. Esters of β-(3,5-di-tert.butyl-4-hydroxyphenyl)-propionic acid with mono- or polyvalent alcohols, such as with methanol, octadecanol, 1,6-hexanediol, ethylene glycol, thiodiethylene glycol, neopentyl glycol, pentaerythritol, tris-hydroxyethyl-isocyanurate.
6. Spiro compounds, such as diphenolic spiro-diacetals or spiro-diketals, such as 2,4,8,10-tetraoxaspiro-[5,5]-undecane substituted in the 3- and 9-position with phenolic radicals, such as 3,9-bis-(3,5-di-tert.butyl-4-hydroxyphenyl)-2,4,8,10-tetraoxaspiro-[5,5]-undecane, 3,9-bis-[1,1-dimethyl-2-(3,5-ditert.-butyl-4-hydroxyphenyl)-ethyl]-2,4,8,10-tetraoxaspiro-[5,5]-undecane.

Particularly preferred phenolic compounds are:
1,3,5-tri-(3,5-di-tert.-butyl-4-hydroxybenzyl)-2,4,6-trimethylbenzene,
pentaerythritol-tetra[3-(3,5-di-tert.-butyl-4-hydroxyphenyl)-propionate],
β-(3,5-di-tert.-butyl-4-hydroxyphenyl)-propionic acid-n-octadecyl ester,
thiodiethylene glycol-β-[4-hydroxy-3,5-di-tert.-butylphenyl]-propionate,
2,6-di-tert.-butyl-4-methyl-phenol, and
3,9-bis-[1,1-dimethyl-2-(3,5-ditert.-butyl-4-hydroxyphenyl)-ethyl]-2,4,8,10-tetraoxaspiro-[5,5]-undecane.

The following may be mentioned as examples of further additives that can be used together with the stabilizer of this invention and the antioxidant:

1. Aminoaryl derivatives, e.g. phenyl-1-naphthylamine, phenyl-2-naphthylamine, N,N'-diphenyl-p-phenylenediamine, N,N'-di-2-naphthyl-p-phenylenediamine, N,N'-di-2-naphthyl-p-phenylenediamine, N,N'-di-sec.-butyl-p-phenylenediamine, 6-ethoxy-2,2,4-trimethyl-1,2-dihydroquinoline, 6-dodecyl-2,2,4-trimethyl-1,2-dihydroquinoline, mono- and dioctyliminodibenzyl, polymerised 2,2,4-trimethyl-1,2-dihydroquinoline. Octylated diphenylamine, nonylated diphenylamine, N-phenyl N'-cyclohexyl-p-phenylenediamine, N-phenyl-N'-isopropyl-p-phenylenediamine, N,N'-di-sec.octyl-p-phenylenediamine, N-phenyl-N'-Sec.-octyl-p-phenylenediamine, N,N'-di-(1,4-dimethylpentyl)-p-phenylenediamine, N,N'-dimethyl-N,N'-di-(sec.-octyl)-p-phenylenediamine, 2,6-dimethyl-4-methoxyaniline, 4-ethoxy-N-sec.-butylaniline, diphenylamineacetone condensation product, aldol-1-naphthylamine and phenothiazine.

With the use of this group, discolouration effects have to be taken into account.

2. UV-Absorbers and light-stabilising agents 2.1. 2-(2'-Hydroxyphenyl)-benzotriazoles, e.g. the 5'-methyl-, 3',5'-di-tert.-butyl-, 5'-tert.-butyl-, 5'-(1,1,3,3-tetramethylbutyl)-, 5-chloro-3',5'-di-tert.-butyl-, 5-chloro-3'-tert.-butyl-5'-methyl-, 3'-sec.-butyl-5'-tert.-butyl-, 3'-α-methylbenzyl-5'-methyl-, 3'-α-methylbenzyl-5'-methyl-5-chloro-, 4'-hydroxy-, 4'-methoxy-, 4'-octoxy-, 3',5'-di-tert.-amyl-, 3'-methyl-5'-carbomethoxyethyl- and 5-chloro-3',5'-di-tert.-amyl-derivative.

2.2. 2,4-bis-(2'-Hydroxyphenyl)-6-alkyl-s-triazines, e.g. the 6-ethyl-, 6-heptadecyl- or 6-undecyl-derivative.

2.3. 2-Hydroxybenzophenones, e.g. the 4-hydroxy-, 4-methoxy-, 4-octoxy-, 4-decyloxy-, 4-dodecyloxy-, 4-benzyloxy-, 4,2',4'-trihydroxy- or 2'-hydroxy-4,4'-dimethoxy-derivative.

2.4. 1,3-bis-(2'-Hydroxybenzoyl)-benzenes, e.g. 1,3-bis-(2'-hydroxy-4'-hexyloxy-benzoyl)-benzene, 1,3-bis-(2'-hydroxy-4'-octyloxy-benzoyl)-benzene or 1,3-bis-(2'-hydroxy-4'-dodecyloxy-benzoyl)-benzene.

2.5. Esters of optionally substituted benzoic acids, e.g. phenylsalicylate, octylphenylsalicylate, dibenzoylresorcin, bis-(4-tert.-butylbenzoyl)-resorcin, benzoylresorcin, 3,5-di-tert.-butyl-4-hydroxybenzoic acid-2,4-ditert.-butylphenyl ester or -octadecyl ester or -2-methyl-4,6-di-tert.-butyl ester.

2.6. Acrylates, e.g. α-cyano-β,β-diphenylacrylic acid-ethyl ester or -isooctyl ester, α-carbomethoxy-cinnamic acid methyl ester, α-cyano-β-methyl-p-methoxy-cinnamic acid methyl ester or -butyl ester. or N-(β-carbomethoxyvinyl)-2-methyl-indoline.

2.7. Nickel compounds, e.g. nickel complexes of 2,2'-thio-bis-[4-(1,1,3,3-tetramethylbutyl)-phenol], such as the 1:1- or 1:2-complex, optionally with additional ligands such as n-butylamine, triethanolamine or N-cyclohexyl-di-ethanolamine, nickel complexes of bis-[2-hydroxy-4-(1,1,3,3-tetramethylbutyl)-phenyl]-sulphone, such as the 2:1-complex, optionally with additional ligands such as 2-ethylcapronic acid, nickeldibytyldithiocarbamate, nickel salts of 4-hydroxy-3,5-ditert.-butylbenzyl-phosphonic acid-monoalkyl esters, such as of methyl, ethyl or butyl esters, nickel complexes of ketoximes, such as of 2-hydroxy-4-methyl-phenyl-undecylketonoxime, nickel-3,5-di-tert.-butyl-4-hydroxybenzoate or nickel-isopropylxanthogenate.

2.8 Sterically hindered amines, e.g. 4-benzoyl-2,2,6,6-tetramethylpiperidine, 4-stearoyloxy-2,2,6,6-tetramethylpiperidine, bis-(2,2,6,6-tetramethylpiperidyl)-sebacate or 3-n-octyl-7,7,9,9-tetramethyl-1,3,8-triazaspiro[4,5]decane-2,4-dione.

2.9. Oxalic acid diamides, e.g. 4,4'-di-octyloxy-oxanilide, 2,2'-di-octyloxy-5,5'-di-tert.-butyl-oxanilide, 2,2'-di-dodecyloxy-5,5'-di-tert.-butyloxanilide, 2-ethoxy-2'-ethyl-oxanilide, N,N'-bis-(3-dimethylaminopropyl)-oxalamide, 2-ethoxy-5-tert.-butyl-2'-ethyloxanilide and the mixture thereof with 2-ethoxy-2'-ethyl-5,4'-di-tert.-butyl-oxanilide, or mixtures of ortho- and para-methoxy- as well as of o- and p-ethoxy-disubstituted oxanilides.

3. Metal deactivators, e.g. oxanilide, isophthalic acid dihydrazide, sebacic acid-bisphenylhydrazide, bis-benzylidene-oxalic acid dihydrazide, N,N'-diacetal-adipic acid dihydrazide, N,N'-bis-salicyloyloxalic acid dihydrazide, N,N'-bis-salicyloylhydrazine, N,N'-bis-(3,5-di-tert.-butyl-4-hydroxyphenylpropionyl)-hydrazine, N-salicyloyl-N'-salicylalhydrazine, 3-salicyloylamino-1,2,4-triazole or N,N'-bis-salicyloyl-thiopropionic acid dihydrazide.

4. Basic co-stabilisers, e.g. alkali metal salts and alkaline-earth metal salts of higher fatty acids, for example Ca-stearate, Zn-stearate, Mg-behenate, Na-ricinoleate or K-palmitate.

5. Nucleation agents, e.g. 4-tert.-butylbenzoic acid, adipic acid or diphenylacetic acid.

6. Phosphites, such as, for example, triphenyl phosphite, diphenylalkyl phosphites, phenyldialkyl phosphites, tri(nonylphenyl) phosphite, trilauryl phosphite, trioctadecyl phosphite, 3,9-di-isodecyloxy-2,4,8,10-tetraoxa-3,9-diphosphaspiro[5,5]-undecane and tri-(4-hydroxy-3,5-di-tert.butylphenyl) phosphite.

Other additives that can be incorporated in the stabilized compositions are thiosynergists such as dilaurylthiodiprionate or distearylthiodipropionate, lubricants such as stearyl alcohol fillers, carbon black, asbestos, kaolin, talcum, glass fibres, pigments, optical brighteners, flameproofing agents and antistatic agents.

The use of the stabilizers of formula I with the above-listed antioxidants is particularly effective for the stabilization of olefin polymers, e.g. polypropylene and copolymers of ethylene and acrylic or methacrylic acid, impact polystyrene and acrylonitrile-butadiene-styrene copolymer. Synergistic effects may occur in using such known additives in combination with the stabilizers of formula I. This is especially true with the UV absorbers and light stabilizers and phosphites.

As was pointed out in the discussion of the background of the invention, the prior art has taught that generally the compounds of the type similar to this invention are used as stabilized against light-induced deterioration. The prior art, however, has not contemplated the piperidinol esters of the higher di and tribasic acids and the unexpected highly superior performance of these compounds. Although the compounds of this invention are generally superior light stabilizers as compared to the corresponding lower acid compounds, their superior performance is especially evident when employed in the fibers that have been subjected to the tentering process. This procedure involves subjecting the fibers to a heat treatment at 121° C (250° F) for 20 to 60 minutes. Since in the fiber manufacture the fibers are usually subjected to same or similar heat treatment, it is of paramount importance for the light stabilizer to be able to protect the fiber against light degradation after such a treatment.

The present invention is further illustrated in the following examples.

EXAMPLE 1

"Dimer Acid" diester of 2,2,6,6-tetramethylpiperidin-4-ol (The "Dimer Acid" used in this example is a $C_{36}$ di-acid derived by the Diels-Alder dimerization of linoleic and/or oleic acid as in Empol 1010, a product of Emery Industries, Cincinnati, Ohio.)

In a 500 ml 3-necked flask equipped with a stirrer, thermometer, $N_2$ inlet and condenser with Dean-Stark trap and drying tube were placed 14.7 g (0.05 moles) of Dimer Acid (approx. mw 565), 7.85 g (0.05 moles) of 2,2,6,6-tetramethylpiperidin-4-ol, 250 ml of xylene, and 1,48 ml (0.005 moles) of Ti(Oipr)$_4$. The reaction mixture was heated to reflux with stirring under nitrogen for 96 hours; then cooled to room temperature. The reaction mixture was treated with 100 ml of water, filtered, and the layers separated with the aid of 700 ml of saturated NaCl solution.

The organic layer was washed with 100 ml of 2N NaOH, three times with 100 ml portions of water, and dried over Mg SO$_4$. During each washing step, the emulsion formation was controlled by the addition of saturated NaCl solution.

The dried organic layer was evaporated under reduced pressure giving the desired diester as yellow oil.

The material was characterized by titration with HClO$_4$ in HOAc giving an equivalent weight of 424 (theory 421) and an elemental analysis as follows:

Calculated for $C_{44}H_{100}O_4 N_2$ F.W. wt. 841

| theory: | C | 7.08 | found: | C | 76.26 |
|---|---|---|---|---|---|
| | H | 11.98 | | H | 11.87 |
| | N | 3.33 | | N | 2.93 |

EXAMPLE 2

Dimethyl Ester of Dimer Acid -

In a 1-liter 3-necked flask equipped with a condenser, therometer, and nitrogen inlet were placed 100 g (.177 moles) of Dimer Acid, 500 ml of absolute methanol and 4.0 g of p-toluene sulfonic acid monohydrate. The reaction mixture was heated under reflux for 2½ hours during which time a second phase developed. The reaction mixture was then cooled to coom temperature and 2.12 g of $Na_2CO_3$ were added with stirring. The reaction mixture was decanted into a separatory funnel and the lower product layer was separated. The separated product was diluted with 250 ml of $CHCl_3$ and the organic solution washed with 250 ml of $H_2O$.

The organic layer was dried over molecular seives (4A) and evaporated under reduced pressure, giving the desired dimethyl ester as a slightly yellow oil which was used in the following reaction.

EXAMPLE 3

Dimer Acid Diester of 2,2,6,6-tetramethylpiperidin-4-ol

In a 1-liter 3-necked flask equipped with a stirrer, thermometer, $N_2$ inlet, and condenser with Dean-Stark Trap and drying tube were placed 92.7 g (.153 moles) of Dimer Acid dimethyl ester, 50.52 g (.32 moles) of 2,2,6,6-tetramethyl piperidin-4-ol, 500 ml of V.M. and P. Naphtha (a commercial aliphatic hydrocarbon solvent of about 125° C b.p.) and .35 g of lithium amide. The reaction mixture was heated under reflux for four hours, during which time 15.1 ml of a 90% methanol-10% Naphtha mixture accumulated in the Dean-Stark Trap. The reaction mixture was then cooled to room temperature and 0.92 g of glacial acetic acid was added, and the mixture was stirred for 10 minutes.

The reaction mixture was transferred to a separatory funnel and washed with 3 - 250 ml portions of water and 10 ml of saturated NaCl and then 250 ml of water. The organic phase was dried over molecular seives (4A) and evaporated under reduced pressure, giving the desired products as a slightly yellow oil.

The product was characterized by an acid value of <1 mg KOH/gm sample (Theory O) and a saponification number of 137.5 mg. KOH/gm (equivalent weight 428.26, theory 424). Titration with $HClO_4$/HOAc gave equivalent weights of 453 and 448 (Theory 424).

EXAMPLE 4

Methyl Ester of Polybasic Acid (The polybasic acid employed in this example is Empol 1054A, a product of Emery Industries, Cincinnati, Ohio. It is a mixture of 4% $C_{18}$ monobasic acid, 55% $C_{36}$ dibasic acid, 35% $C_{54}$ tribasic acids, and 6% polybasic acid. The functionality of the polybasic acid portion of the mixture has been found to be greater than 3.0. The estimated functionality of Empol 1054, based in part on TGA analyses, is 2.65–2.75. The acid value, by tentative specifications, is 186–196 mg KOH/gm which indicates an equivalent weight of 286.3–301.7.)

In a 1-liter 3-necked flask equipped with a stirrer, thermometer, condenser and nitrogen inlet were placed 100 g of Polybasic Acid (Empol 1054A) (0.340 equivalents), 500 ml of absolute methanol, and 4.0 g (0.02 moles) of p-toluene sulfonic acid monohydrate. The reaction mixture, initially homogeneous, was heated to reflux under nitrogen for 4 hours. During this time, a second heavier phase separated. At the end of the reflux, the reaction mixture was cooled to room temperature and decanted into a 1-liter separating funnel. The lower product layer was separated, diluted with 100 ml of ether, the ether solution washed with 2 - 250 ml portions of water and dried over 4A molecular seives. The upper methanol layer was treated with 2.1 g of $Na_2CO_3$ and evaporated under reduced pressure. The residue was dissolved in 100 ml of ether, the ether solution washed with 2 - 125 ml portions of water, and dried over 4A molecular seives.

The two ether solutions were evaporated to dryness and combined yielding 100.5 g (97.5%) of the desired methyl ester. This compound had saponification number of about 133 mg. KOH/g of sample.

EXAMPLE 5

Poly (2,2,6,6-tetramethyl piperidyl-4) ester of Polybasic acid

In a 1-liter 3-necked flask equipped with a stirrer, nitrogen inlet, thermometer, and condenser with Dean-Stark Trap and drying tube were placed 92.3 g (0.3 equivalents) of the methyl ester of Polybasic Acid prepared in Example 4, 49.54 g (.315 moles) of 2,2,6,6-tetramethyl piperidin-4-ol, 500 ml of V.M. and P. Naphtha, and 0.35 g (01015 moles) of lithium amide. The reaction mixture was heated under reflux for 3 hours during which time 14.0 ml of a 90% methanol - 10% Naphtha mixture was separated in the Dean-Stark Trap, which was removed. During the next 1½ hours of reflux, 100 ml of distillate were removed. The reaction mixture was then cooled and 1.18 g of glacial acetic acid were added, and the reaction mixture was stirred for ½ hour. The reaction mixture was transferred to a 1-liter separatory funnel and washed with 250 ml of water, which resulted in an emulsion, which was broken by the addition of 50 ml of saturated sodium chloride solution and 100 ml of ether. The organic layer was separated with difficulty, washed with 250 ml of saturated sodium chloride, and dried over 4A molecular seives. The aqueous layer from the second washing was extracted with 2 - 100 ml portions of ether, and the ether extracts combined and dried over 4A molecular seives. The dried ether solutions were combined and evaporated under reduced pressure, yielding the desired ester as a yellow oil.

Elemental analysis: calculated for an empirical formula of $(C_{27}H_{50}O_2N)n$

| calc. | C | 77.08 | Found | C | 77.29 |
|---|---|---|---|---|---|
| | H | 11.98 | | H | 12.07 |
| | N | 3.27 | | N | 3.73 |

Equivalent weight by titration with $HCLO_4$/HOAc; 440 (Theory from above empirical formula 420.7).

EXAMPLE 6

Dimer Acid Diester of 2,6-diethyl-2,3,6-trimethylpiperidin-4-ol

By substituting in Example 3 for the 2,2,6,6-tetramethylpiperidin-4-ol an equivalent amount of 2,6-diethyl-2,3,6-trimethylpiperidin-4-ol is produced the above named compounds which is a yellow oil. It's elemental analysis was as follows:
Calc. for $C_{60}H_{108}N_2O_4$ F.W. 940

| Calc. | C | 78.20 | Found | 78.20 |
|---|---|---|---|---|
| | H | 11.81 | | 12.20 |
| | N | 3.04 | | 2.92 |

EXAMPLE 7
Dimer Acid Diester of 1,2,2,6,6-pentamethyl piperidin-4-ol

By substituting in Example 3 for the 2,2,6,6-tetramethyl piperidin-4-ol an equivalent amount of 1,2,2,6,6-pentamethylpiperidin-4-ol is produced the above named compound which is a yellow oil.

EXAMPLE 8
Artificial Light Exposure Test

Deterioration of most polymers caused by ultraviolet light is so slow at ambient temperatures, even in the absence of stabilizers, that testing of the effects of stabilizers generally must be conducted either at higher temperatures or in an accelerated artificial light exposure device in order to yield results in a convenient period of time. The tests conducted on polymers using an aritificial light exposure device is described below:

SAMPLE PREPARATION

Polypropylene powder (Profax 6401, Hercules) (100 parts by weight) was blended with Pentaerythritol Tetrakis [3-(3', 5',-di-t-butyl-4'-hydroxyphenyl) propionate] (Irganox 1010) (0.1 parts by weight), calcium sterate 0.1 parts by weight) and the indicated amount of light stabilizing additive. The powder was extruder compounded into pellets, and the pellets spun into 750/150 or 204/34 denier multifilament. The multifilament was knitted into a fabric, and the knitted fabric mounted on cardboard frames.

TESTING METHOD

Some of the frames were placed in an oven at 121° C (250° F) for 20 minutes or 60 minutes (Tentering Procedure). The untentered and tentered knitted samples were exposed in the Carbon Arc Weatherometer without water spray. At intervals the fibers were tested for percent retention of tensile strength vs. an unexposed sample, and failure was taken at 50% retention of tensile strength. The results are shown in the following tables.

Table I
Effect of Tentering on Fiber

| Composition: | Profax 6401 | 100 | parts by wt. |
|---|---|---|---|
| | Antioxidant A* | 0.1 | parts by wt. |
| | Calcium stearate | 0.1 | parts by wt. |
| | Light Stabilizing Additive | | as indicated |

750/150 Denier Fiber

| | | Hours to 50% retention of tenacity or % retention at 310 hrs. | |
|---|---|---|---|
| Additive | Concentration parts by wt. | no tentering | 20 min tentering |
| Light Stab.[1] | 0.1 | 200 | 125 |
| light Stab. | 0.25 | 77% | 205 |
| Compd. Ex. 3 | 0.25 | 295 | 275 |
| Compd. Ex. 3 | 0.437[2] | 87% | 85% |

*Antioxidant A is Pentaerythritol Tetrakis [3-(3',5'-di-t-butyl-4-hydroxy phenyl)propionate]

204/34 Denier Fiber

| | | Hrs to 50% retention of tenacity | | | % Loss of stabilizer effectiveness |
|---|---|---|---|---|---|
| Additive | Concentration | no tent | 20 min tent | 60 min tent | after 20 min. tentering |
| Light Stab.[1] | 0.25 | 525 | 257 | 220 | 51% |
| Light Stab. | 0.5 | 600 | 360 | — | 45% |
| Compd of Ex. 3 | 0.25 | 325 | 305 | — | 6% |
| Compd of Ex. 3 | 0.437[2] | 450 | 360 | 305 | 20% |
| Compd of Ex. 3 | 0.874[3] | 410 | 410 | — | 0 |

[1]Prior art light stabilizer bis(2,2,6,6-tetramethyl piperidyl-4)sebacate
[2]Molar concentration equivalent to 0.25% sebacate diester
[3]Molar concentration equivalent to 0.5% sebacate diester Other hindered phenolic antioxidants may be used in place of pentaerithritol-tetrakis [3,5-di-t-butyl-4-hdroxyphenyl)] propionate in the composition of Example 13, such as di-n-octadecyl α-(3-t-butyl-4-hydroxy-4-methylbenzyl)malonate, 2,4-bis(n-octylthio)-6-(3,4-di-t-butyl-4-hydroxyaniline)-1,3,5-triazine, octadecyl 3-(3',5'-di-t-butyl-4'hydroxyphenyl) propionate, dioctadecyl(3,5-di-t-butyl-4-hydroxybenzyl)phosphonate, tris-(3,5,di-t-butyl-4-hydroxy-benzyl)tris-(3,5-di-tert-butyl-4-hydroxybenzyl)isocyanurate, and 2,4,6-tris(3,5-di-tert-butyl-4-hydroxybenzyl)-1,3,5-tri-methylbenzyl.

The following UV absorbers are included in the formulation at 0.01 to 2%:
a. 2(2'-hydroxy-3',5'-di-t-butylphenyl)-5-chlorobenzotriazole
b. 2-hydroxy-4-methoxy-5-sulfobenzophenone trihydrate
c. 2-hydroxy-4-n-octoxybenzophenone
d. [2,2'-thiobis(4-t-octylphenolate)]-n-butylamine nickel II
e. p-octylphenyl salicylate
f. 2,2'-dihydroxy-4,4'-dimethoxybenzophenone
g. 2(2'-hydroxy-5'-methylphenyl)-benzotriazole.

EXAMPLE 9

High impact polystyrene resin containing elastomer (i.e., butadiene-styrene) is stabilized against loss of elongation properties due to exposure to ultraviolet light by incorporation of 0.2% by weight of Dimer Acid diester of 2,6-diethyl-2,3,6-trimethyl piperidin-4-ol.

The unstabilized resin is dissolved in chloroform and the stabilizer then added, after which the mixture is cast on a glass plate and the solvent evaporated to yield a uniform film which, upon drying, is removed and cut up, and then pressed for 7 minutes at a temperature of 163° C and a pressure of 2,000 pounds per square inch into sheet of uniform thickness (25 mil). The sheets are then cut into strips approximately 4 × 0.5 inches. A portion of these strips is then measured for percent of elongation in the Instron Tensile Testing Apparatus (Instron Engineering Corporation, Quincy, Massachusetts). The remaining portions of the strips are placed in an FS/BL chamber according to Example 6(B) except that the sample are mounted and white cardboard stock and the time to 50% reduction in elongation is measured. The stabilized polystyrene resin retains its original elongation loger than the unstabilized resin.

EXAMPLE 10

Unstabilized linear polyethylene is solvent blended in methylene chloride with 0.5% by weight of the substrate of the Compound of Example 5 and then vacuum dried. The resin is then extrusion compounded on a 1 inch 24/1=L/D extruder, melt temperature 450° F (232° C) and pressed for 7 minutes at a temperature of 163° C and a pressure of 2,000 psi into a sheet of uniform thickness of 100 mil. The sheets are then cut into plaques of 2 inch × 2 inch. The plaques are then exposed in an FS/BL exposure device and color measurements made periodically using a Hunter Color Difference Meter Model D25. Polyethylene stabilized with the above compound is found to be much more stable than the unstabilized polyethylene or the polyethylene stabilized only with an antioxidant.

EXAMPLE 11 a. A stabilized polyamide (nylon 6,6) is prepared by incorporating therein 0.1% of $C_{54}$ Trimer acid triester of 2,2,6,6-tetramethyl piperidin-4-ol. The light stability of the stabilized composition is superior to that of an unstabilized polyamide.

b. A stabilized polyphenylene oxide polymer (prepared by polymerizing 2,6-dimethylphenol is prepared by incorporating therein 0.5% by weight of $C_{36}$ Dimer acid diester of 1,2,2,6,6-pentamethylpiperidin-4-ol. The stabilized compositions resists embrittlement due to exposure to ultraviolet light longer than one which does not contain the stabilizer.

c. A stabilized crystalline polystyrene is prepared by incorporating therein 0.1% weight of $C_{36}$ Dimer Acid diester of 1,2,2,6,6-pentamethyl piperidin-4-ol. The stabilized composition resists embrittlement due to exposure to ultraviolet light longer than one which does not contain the stabilizer.

d. A stabilized resin consisting of a copolymer of an alpha olefin with an $\alpha$, $\beta$-unsaturated acid especially a copolymer of ethylene and acrylic acid or methacrylic acid, unneutralized or partially neutralized with sodium or zinc ions, is prepared by extrusion compounding 0. 0.01–2% especially 0.05–0.5% by weight of the $C_{36}$ dimer acid diester of 2,2,6,6-tetramethyl piperidin-4-ol. The stabilized composition is formed into films and exposed to ultraviolet light or sunlight. The stabilized composition resists embrittlement due to exposure to ultraviolet light longer than one which does not contain the stabilizer.

What is claimed is:

1. A piperidyl ester having the formula

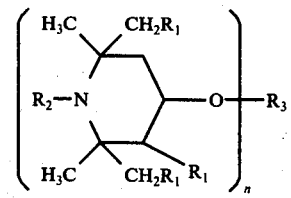

wherein $R_1$ is hydrogen or a lower alkyl group of 1 to 5 carbon atoms, $R_2$ is hydrogen, oxyl, alkyl having 1–12 carbon atoms, alkoxyalkyl of 2 to 21 carbons, alkenyl of 3 to 6 carbons, alkinyl of 3 to 6 carbons benzyl or benzyl substituted by alkyl groups of 1 to 4 carbons, or acyl derived from a saturated or unsaturated aliphatic acid of 1 to 4 carbons or aliphatic, cycloaliphatic or aromatic carbamic acid of the formula —CO—NH—R or aliphatic, cycloaliphatic or aromatic carbonic acid half ester of the formula — COOR wherein R is alkyl of 1 to 6 carbons, $n$ is an integer of 2 or 3;

when $n$ = 2, $R_3$ is a diacyl group derived from a straight or branched chain aliphatic or alicyclic, saturated or unsaturated carboxylic acid, having 36 carbon atoms when $n$ is 3, $R_3$ is a tri-acyl group derived from a straight or branched chain aliphatic or alicyclic saturated or unsaturated carboxylic acid having from 37 to 54 carbon atoms.

2. A compound of claim 1 wherein $n$ is 2, $R_1$ is hydrogen or methyl, $R_2$ is hydrogen, lower alkyl or lower acyl and $R_3$ is diacyl group derived from an alicyclic dicarboxylic acid which contains alkyl, alkenyl, carboxyalkylene and/or carboxyalkenylene substituents on the unsaturated six membered alicyclic ring, said acid having 36 carbon atoms.

3. A compound of claim 1 wherein $n$ is 3, $R_1$ is hydrogen or methyl, and $R_3$ is a triacyl group derived from an alicyclic tricarboxylic acid which contains alkyl and carboxyalkyl substituents on the unsaturated six-membered alicyclic rings, said acid having 37 to 54 carbon atoms and two alicyclic rings.

4. A mixture of compounds of claim 1, which consists of (a) predominantly a compound wherein $n$ is 2 and $R_3$ is a diacyl group having 36 carbon atoms and (b) a substantial member of a compound wherein $n$ is 3 and $R_3$ is a triacyl group having 54 carbon atoms.

5. A mixture of claim 4, wherein $R_1$ is hydrogen or methyl.

6. The compound of claim 1 which is $C_{36}$ dimer acid diester of 2,2,6,6-tetramethyl piperidin-4-ol.

7. The compound of claim 1 which is poly(2,2,6,6-tetramethylpiperidyl-4) ester of polybasic acid.

8. The compound of claim 1 which is $C_{36}$ dimer acid diester of 1,2,2,6,6-tetramethylpiperidin-4-ol.

9. A composition of matter comprising a polymeric material subject to light deterioration stabilized with a compound of claim 1.

10. A composition of claim 9 wherein the stabilizer is a compound of the formula

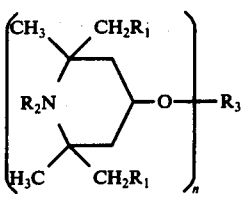

wherein $R_1$ is hydrogen or methyl, $R_2$ is hydrogen, lower alkyl or lower acyl, $n$ is 2 and $R_3$ is a diacyl group derived from an alicyclic dicarboxylic acid which contains alkyl, alkenyl, carboxyalkylene and/or carboxyalkenylene substituents on the unsaturated six membered alicyclic ring, said acid having 36 carbon atoms.

11. A composition of claim 10 wherein $n$ is 3 and $R_3$ is a triacyl group derived from an alicyclic tricarboxylic acid which contains alkyl and carboxyalkyl substituents on the unsaturated six-membered alicyclic rings, said acid having 37 and 54 carbon atoms and two alicyclic rings.

12. A composition of claim 11 wherein the stabilizer is the $C_{36}$ dimeric acid diester of 2,2,6,6-tetramethyl-piperidin-4-ol.

13. A composition of claim 9 wherein the polymer is polyolefin.

14. A composition of claim 9 wherein the stabilizer is a mixture of compounds containing
  a. predominantly a compound wherein $n$ is 2 and $R_3$ is a diacyl group having 36 carbon atoms, and
  b. a substantial amount of a compound wherein $n$ is 3 and $R_3$ is a triacyl group having 54 carbon atoms.

15. A composition of claim 14 wherein the mixture contains
  a. $C_{36}$ dibasic acid ester of 2,2,6,6-tetramethyl piperidin-4-ol,
  b. $C_{54}$ tribasic acid ester of 2,2,6,6-tetramethylpiperidin-4-ol.

16. A composition of claim 15 wherein the polymer is polypropylene.

* * * * *